(12) United States Patent
Humbert et al.

(10) Patent No.: US 11,458,179 B2
(45) Date of Patent: Oct. 4, 2022

(54) METHOD FOR OBTAINING AN EXTRACT ENRICHED IN ROSMARINIC ACID FROM FRESH PLANT MATERIAL

(71) Applicants: ROBERTET SA, Grasse (FR); PLANTES AROMATIQUES DU DIOIS, Vercheny (FR)

(72) Inventors: Marina Humbert, Grasse (FR); Michel Meneuvrier, Aouste sur Sye (FR); Thomas Ughetto, Grasse (FR); Sophie Lavoine, Mouans-Sartoux (FR)

(73) Assignees: PLANTES AROMATIQUES DU DIOIS, Vercheny (FR); ROBERTET SA, Grasse (FR)

( * ) Notice: Subject to any disclaimer, the term of this patent is extended or adjusted under 35 U.S.C. 154(b) by 0 days.

(21) Appl. No.: 16/969,432

(22) PCT Filed: Feb. 14, 2019

(86) PCT No.: PCT/EP2019/053710
§ 371 (c)(1),
(2) Date: Aug. 12, 2020

(87) PCT Pub. No.: WO2019/158654
PCT Pub. Date: Aug. 22, 2019

(65) Prior Publication Data
US 2021/0000901 A1 Jan. 7, 2021

(30) Foreign Application Priority Data
Feb. 15, 2018 (FR) ...................... 1870166

(51) Int. Cl.
| | | |
|---|---|---|
| *A61K 36/53* | (2006.01) | |
| *A23L 33/105* | (2016.01) | |
| *A61K 8/9789* | (2017.01) | |
| *A61K 8/37* | (2006.01) | |
| *A61K 31/216* | (2006.01) | |
| *A61K 36/534* | (2006.01) | |
| *A61K 36/537* | (2006.01) | |
| *A61Q 19/08* | (2006.01) | |

(52) U.S. Cl.
CPC ............ *A61K 36/53* (2013.01); *A23L 33/105* (2016.08); *A61K 8/37* (2013.01); *A61K 8/9789* (2017.08); *A61K 31/216* (2013.01); *A61K 36/534* (2013.01); *A61K 36/537* (2013.01); *A61Q 19/08* (2013.01); *A23V 2002/00* (2013.01); *A61K 2236/15* (2013.01); *A61K 2236/37* (2013.01); *A61K 2236/39* (2013.01)

(58) Field of Classification Search
None
See application file for complete search history.

(56) References Cited

U.S. PATENT DOCUMENTS

| | | |
|---|---|---|
| 4,354,035 A | 10/1982 | Christ et al. |
| 9,913,874 B2 | 3/2018 | Dermo-Cosmetique et al. |
| 2012/0201935 A1 | 8/2012 | Krohn et al. |
| 2016/0243186 A1* | 8/2016 | Mandeau ............. A61K 8/9789 |

FOREIGN PATENT DOCUMENTS

| | | |
|---|---|---|
| CN | 101332229 A | 12/2008 |
| CN | 101439066 A | 5/2009 |
| CN | 104490994 A | 4/2015 |
| KR | 1020080111200 A | 12/2008 |
| WO | 9733596 A1 | 9/1997 |
| WO | 2009005791 A1 | 1/2009 |
| WO | 2015/040135 | 3/2015 |

OTHER PUBLICATIONS

Peev et al. (2011) Chemical Engineering Research and Design (2011) 89: 2236-2243. (Year: 2011).*
Raskin et al. (2004) Current Pharmaceutical Design, 10: 3419-3429. (Year: 2004).*
Revilla et al. (1998) J. Agric. Food Chem. 46: 4592-4597. (Year: 1998).*
Salinas et al. (2012) J. Agric. Food Chem. 60: 10920-10929. (Year: 2012).*
PCT, International Search Report and Written Opinion; International Application No. PCT/EP2019053710, dated Apr. 1, 2019 (11 pages).
PCT, English Translation of International Search Report; International Application No. PCT/EP2019053710, dated Apr. 1, 2019 (3 pages).
Dobravalskyte,Le bioraffinage de Myrrhis odorata, Tussilago farfara et Calamintha grandiflora pour la production d'arômes et d'antioxydants, Nov. 25, 2013, p. 1-193.
Kamdem et al.,Antioxidant activity, genotoxicity and cytotoxicity evaluation of lemon balm (*Melissa officinalis* L.) ethanolic extract: Its potential role in neuroprotection, Industrial Crops and Products, Nov. 2013, p. 26-34, vol. 51.

(Continued)

*Primary Examiner* — Russell G Fiebig
(74) *Attorney, Agent, or Firm* — FisherBroyles, LLP; Susan M. Oiler (57) ABSTRACT

Methods for obtaining an extract enriched in rosmarinic acid from fresh plant material selected from the fresh aerial parts, flowering tops, flowers and/or leaves of plants from the family Lamiaceae, Araliaceae, Boraginaceae, Apiaceae, Poaceae and Malvaceae. The methods include steam bleaching the plant material followed by continuous expression with at least one compression screw, under pressure of between 4 and 10 bar from which the sap (liquid co-product) is recovered. Then, the sap is filtered to produce a clarified sap and is subsequently atomized to obtain a granulated or finely powdered extract containing at least 5% of rosmarinic acid in weight relative to the total weight of the extract. Compositions having such an extract as an active agent are disclosed. The compositions are used in the food, cosmetic, nutraceutical and pharmaceutical fields.

6 Claims, 2 Drawing Sheets

(56) References Cited

OTHER PUBLICATIONS

Lin et al., Antioxidant, anti-proliferative and cyclooxygenase-2 inhibitory activities of ethanol extracts from lemon balm (*Melissa officinalis* L.) leaves, LWT, Nov. 2012, p. 1-7, vol. 49—Issue 1.
Awad et al., Bioassay-guided fractionation of lemon balm (*Melissa officinalis*L.) using an in vitro measure of GABA transaminase activity, Phytotherapy Research, Jan. 22, 2009, p. 1075-1081, vol. 23—Issue 8.
Canadanovic-Brunet et al., Radical scavenging, antibacterial, and antiproliferative activities of *Melissa officinalis* L. extracts, Journal of Medicinal Food, Mar. 24, 2008, p. 133-143, vol. 11—Issue 1.
Barros et al., Phenolic profiles of cultivated, in vitro and commercial samples of *Melissa officinalis* L. infusions, Food Chemistry, Jan. 1, 2013, p. 1-8, vol. 136—Issue 1.
Arceusz et al., Quality consistency evaluation of *Melissa officinalis* L. commercial herbs by HPLC fingerprint and quantification of selected phenolic acids, Journal of Pharmaceutical and Biomedical Analysis, Deptember 2013, p. 215-220, vol. 83.
Nicolai et al., Antioxidant activity and rosmarinic acid content of ultrasound-assisted ethanolic extracts of medicinal plants, Measurement, Jul. 2016, p. 328-332, vol. 89.
Dastmalchi et al., Chemical composition and in vitro antioxidative activity of a lemon balm (*Melissa officinalis* L.) extract, LWT-Food Science and Technology, Apr. 2008, p. 391-400, vol. 41—Issue 3.
Boyadzhiev et al., Extraction and liquid membrane preconcentration of rosmarinic acid from lemon balm (*Melissa officinalis* L.), Separation Science and Technology, Apr. 2006, p. 877-886, vol. 41—Issue 5.
Search Report,CN Application No. 2019800133273, dated Jul. 6, 2022, 1 page.
Office Action, CN Application No. 2019800133273, dated Jul. 14, 2022, 6 pages.

\* cited by examiner

METHOD FOR OBTAINING AN EXTRACT ENRICHED IN ROSMARINIC ACID FROM FRESH PLANT MATERIAL

CROSS-REFERENCE TO RELATED APPLICATIONS

The present invention is filed under 35 U.S.C. § 371 as the U.S. national phase of International Patent Application No. PCT/EP2019/053710, filed Feb. 14, 2019, which designated the United States and which claims the benefit of French Patent Application No. 1870166 filed Feb. 15, 2018, which is hereby incorporated in its entirety including all tables, figures, and claims.

The present invention concerns the field of extraction of plant material. More specifically, it concerns a method for obtaining an extract enriched in rosmarinic acid from fresh plant material, the extract thus obtained, a composition comprising such an extract as well as the uses of a composition comprising such an extract.

In recent decades, there has been a growing trend towards the consumption of natural products. In particular, there is a strong demand for the development of environmentally friendly extraction processes that reduce energy consumption, use alternative solvents and favour renewable plant resources, while guaranteeing a quality product or extract.

Natural ingredients from co-products are growing in popularity due to developments in recycling procedures applied to pure compounds. One of the major challenges of the food industry is the exploitation of co-products as new ingredients using green technologies at a reduced cost.

It is indeed well known that plant materials such as plants are a source of compounds of interest.

The by-products obtained during the transformation of plants, generally not used, can also represent a resource of bioactive phytochemical compounds, aromatics or antioxidants. Thus, by-products (i.e. non-volatile compounds, solid and liquid co-products), which are obtained by various distillation techniques, can be used or upgraded to improve the commercial feasibility of producing bioactive compounds from different plants.

For example, from Diana Dobravalskyte's thesis ("Le bioraffinage de *Myrrhis odorata, Tussilago farfara* et *Calamintha grandiflora* pour la production d'arômes et d'antioxydants, 2013"), we know about the recycling of co-products from dry plants after hydrodistillation.

The transformation process disclosed is nevertheless carried out from a dry plant and allows hydrodistillation by-products to be obtained, through various in vitro tests using different solvents, to evaluate their antioxidant properties.

Concerning the extraction methods of phenolic compounds and specifically of rosmarinic acid from *Melissa officinalis* L., known for their antioxidant properties, the conventional techniques use preferably organic and/or aqueous solvents, generally at atmospheric pressure, such as hydrodistillation or maceration (Kamdem et al. "Antioxidant activity, genotoxicity and cytotoxicity evaluation of lemon balm (*Melissa officinalis* L.) ethanolic extract: Its potential role in neuroprotection", 2013; Lin et al. "Antioxidant, antiproliferative and cyclooxygenase-2 inhibitory activities of ethanol extracts from lemon balm (*Melissa officinalis* L.) leaves", 2012; patent document U.S. Pat. No. 4,354,035; Awad et al. "Bioassay-guided fractionation of lemon balm (*Melissa officinalis* L.) using an in vitro measure of GABA transaminase activity", 2009; Canadanovic-Brunet et al. "Radical scavenging, antibacterial, and antiproliferative activities of *Melissa officinalis* L. extracts, 2008), an infusion (Barros et al. "Phenolic profiles of cultivated, in vitro and commercial samples of *Melissa officinalis* L. infusions", 2013), Soxhlet extraction, batch extraction, sonication-assisted extraction (Arceusz et al. "Quality consistency evaluation of *Melissa officinalis* L. commercial herbs by HPLC fingerprint and quantification of selected phenolic acids", 2013) or ultrasound ("Antioxidant activity and rosmarinic acid content of ultrasound-assisted ethanolic extracts of medicinal plants", 2016).

The most commonly used solvent systems for the extraction of rosmarinic acid are water, ethanol or aqueous ethanol, methanol or aqueous methanol; ethyl acetate can also be used for extraction.

In addition, extraction is usually done from the dried leaves reduced to powder form.

For example, different compositions are known comprising extracts containing rosmarinic acid obtained from dried plant material such as medicinal granules containing an extract of *Radix Notoginseng* (CN101439066), a functional food and a pharmaceutical composition comprising an extract of *Salvia miltiorrhiza* for preventing thrombus (KR20080111200) or an extract of the plant *Prunella vulgaris* containing an extract of total phenolic acid (CN101332229).

Other extraction techniques for these compounds use higher pressures and/or temperatures such as supercritical fluid extraction, microwave assisted extraction, accelerated solvent extraction, MSLE (Medium pressure Solid Liquid Extraction), Dastmalchi et al. "Chemical composition and in vitro antioxidative activity of a lemon balm (*Melissa officinalis* L.) extract", 2008) or a "pertraction" (or liquid membrane) process (Boyadzhiev et al. "Extraction and liquid membrane preconcentration of rosmarinic acid from lemon balm (*Melissa Officinalis* L.)", 2006).

These different techniques have already been used alone or in combination for the extraction of rosmarinic acid from lemon balm. As rosmarinic acid has not been extracted from the same raw material, the initial concentration of rosmarinic acid may therefore vary from one material to another. Nevertheless, the results obtained are generally between 0.5 and 5% of extracted rosmarinic acid.

Pressure extraction processes are also known. For example, patent document WO2015040135 discloses a process for obtaining a juice from fresh plants, in which said fresh plants, excluding seeds alone, are subject to a solvent-free thermomechanical treatment, followed by a juice recovery operation. Under the more specifically described conditions, the extrusion of thawed fresh aerial parts (20 h at 2° C.) of lemon balm (*Melissa officinalis* L.) allows a juice to be obtained with nearly 50% yield and containing 6.5% of dry matter. This material contains, among other things, rosmarinic acid. The content of rosmarinic acid in the dry matter extracted by extrusion, with no organic solvent, is 2.4% (w/w).

In view of the above, one problem that the invention proposes to solve is to recover a plant in its entirety, creating as little waste as possible and using the co-products. The method developed according to the invention makes it possible to obtain a deodorised extract, in the form of a granulated powder and enriched with rosmarinic acid, from fresh plant material not deteriorated by drying or grinding. This is a solvent-free method. The extracts thus obtained can be advantageously used in particular for the antioxidant properties of rosmarinic acid.

The first objective of the invention is therefore a method for obtaining an extract enriched in rosmarinic acid from fresh plant material selected from the fresh aerial parts, flowering tops, flowers and/or leaves of plants from the family Lamiaceae, Araliaceae, Boraginaceae, Apiaceae, Poaceae and Malvaceae, characterised in that it comprises the following successive steps:

1) steam bleaching of said plant material;

2) continuous expression with at least one compression screw, under pressure between 4 and 10 bar, of the plant material bleached in 1) with recovery of the sap (liquid co-product);

3) filtering the recovered sap in 2) and recovering a clarified sap; and 4) atomisation of the clarified sap in 3), to obtain a granulated or finely powdered extract containing at least 5% rosmarinic acid in weight relative to the total weight of the extract.

In addition, the second objective of the invention is a granulated or finely powdered, (preferably granulated), extract containing at least 5% rosmarinic acid in weight with respect to the total weight of the extract obtained through the method according to the invention.

Another objective of the invention is a composition comprising, in a physiologically acceptable medium, an extract obtainable through the process according to the invention from fresh plant material selected from the fresh aerial parts, flowering tops, flowers and/or leaves of plants of the Lamiaceae family.

Finally, the last objective of the invention is the use of a composition according to the invention in the food and cosmetic fields, or a composition according to the invention for its use as a nutraceutical or medicinal product in humans and/or animals.

In this description, unless otherwise specified, it is understood that, when an interval is given, it includes the upper and lower limits of that interval.

The invention and the advantages deriving therefrom will be better understood by reading the following description and the non-limiting methods of implementation that follow, written in relation to the appended figures in which.

The invention relates to a method for obtaining an extract enriched in rosmarinic acid from fresh plant material selected from the fresh aerial parts, flowering tops, flowers and/or leaves of plants from the family Lamiaceae, Araliaceae, Boraginaceae, Apiaceae, Poaceae and Malvaceae, preferably Lamiaceae.

Rosmarinic acid (of the following formula) is a polyphenol derived from an ester of caffeic acid. It exists as cis and trans isomers; the trans isomer of rosmarinic acid is the natural isomer, which when exposed to daylight changes to the cis isomer.

Fresh or moist plant material means a living organism belonging to the plant kingdom which comprises at least 70% of its total weight in water, e.g. a water content of 80-90%, conventionally about 85% water, before or after loss through desiccation, especially through harvesting.

Advantageously, the plant matter extracted is essentially organically grown.

Preferably, the extracted plant material is selected from sage (*Salvia* ssp.), borage (*Borago officinalis* L.), Java tea (*Orthosiphon aristatus*), ivy (*Hedera Helix* L.), perilla (*Perilla frutescens*), white nettle (*Lamium album*), *Coleus* (of the genus *Coleus, Solenostemon* or *Plectranthus*), rosemary (*Rosmarinus officinalis*), lavender (*Lavandula* ssp), thyme (*Thymus vulgaris* L.), small-leaved linden (*Tilia cordata* Mill.), orchard grass (*Dactylis glomerata* L.), fescue (*Festuca rubra* L.), mountain brome (*Bromus inermis* and *Bromus marginatus*), oregano (*Origanum vulgare*), Lycope d'Europe (*Lycopus europaeus*), common self-heal (*Prunella vulgaris*), mint (*Mentha piperita*), hyssop (*Hyssopus officinalis* L.), basil (*Ocimum basilicum* L.), summer savory (*Satureja hortensis* L.), lemon balm (*Melissa officinalis* L.).

More preferably, the plant material extracted is chosen from sage (*Salvia* ssp), rosemary (*Rosmarinus officinalis*), oregano (*Origanum vulgare*), mint (*Mentha piperita*), summer savory (*Satureja hortensis* L.), lemon balm (*Melissa officinalis* L.), even more preferably from rosemary, oregano or lemon balm.

Even more preferably, the plant material extracted is lemon balm (*Melissa officinalis* L.).

The freshly picked plant material is fragile and can be kept in the same state for a maximum of a few hours, e.g. from a few minutes up to 5 hours, e.g. 1, 2, 3, 4 or 5 hour(s), and is preferably used as soon as possible within 5 hours after harvesting, otherwise it will deteriorate and lose some or all of its properties.

The use of fresh plant material advantageously avoids a drying stage, which can be energy consuming and/or which can lead to a deterioration of the colour (oxidation), and the degradation of certain molecules potentially of interest such as rosmarinic acid.

The method according to the invention is used to obtain an extract enriched in rosmarinic acid from the whole fresh plant material, or advantageously from the fresh aerial parts, flowering tops, flowers and/or leaves.

According to the invention, the method comprises the following successive steps:

1) steam bleaching, preferably for less than 2 hours, of the said plant material;

2) continuous expression (or pressing) with at least one compression screw, under pressure between 4 and 10 bar, of the plant material bleached in 1) with recovery of the sap (liquid co-product);

3) filtering the recovered sap in 2) and recovering a clarified sap; and 4) atomising the clarified sap in 3) to obtain a granulated or finely powdered extract containing at least 5% (w/w) rosmarinic acid in weight relative to the total weight of the extract.

Bleaching is a superficial heat treatment lasting a few minutes, at a temperature between 70° C. and 100° C., intended to destroy the enzymes likely to alter the fresh raw materials. Bleaching reduces the initial microbial load by deactivating heat-sensitive microorganisms. The temperatures used are lethal to yeast as well as to most moulds and aerobic microorganisms.

Bleaching is preferably carried out at atmospheric pressure (around 1 bar) at a temperature of 100° C.

Bleaching is carried out for a period lasting between a few minutes and 2 hours, preferably less than 2 hours, e.g. 1 minute, 10 minutes, 30 minutes, up to 1 hour, more preferably 10 minutes.

The bleaching stage produces a plant material that is advantageously deodorised.

Such a short steam treatment step also preserves and conserves the antioxidant molecules of interest such as rosmarinic acid.

The bleached and deodorised plant material is then continuously pressed with at least one compression screw, under a pressure between 4 and 10 bar, preferably between 5 and 6 bar, e.g. around 6 bar.

The pressing stage is preferably carried out at a temperature between 40° C. and 80° C., preferably at a temperature of around 60° C.

The expression (or pressing) is preferably carried out with a compression screw, at a power of at least 7.5 kW.

As a non-limiting example, the compression screw advantageously used has dimensions of around 3.5 meters×0.9 meters×1.8 meters and a weight of 1700 kg.

Continuous expression under pressure results in a residual cake of plant material (solid co-product) for compost and a sap (liquid co-product) which is recovered.

The liquid sap thus recovered is then filtered, preferably at 100 μm. More preferably, the filtration process is a rotary filtration process carried out with a 100 μm self-cleaning filter. Advantageously, the filtration process has a flow rate of less than 10 m$^3$/h.

After filtration, a mud for composting is thus separated from the clarified plant material sap that is recovered.

The clarified (liquid) sap is finally atomised to obtain a granulated or finely powdered, preferably granulated, extract containing at least 5% (w/w) rosmarinic acid in weight relative to the total weight of the extract.

Advantageously, 5-10% of the total weight of the extract thus obtained represents rosmarinic acid.

The saps (liquid saps) from fresh plants have a high-water content, which gives them the ability to be atomised. Advantageously, this is the case with lemon balm sap.

Atomisation consists of dehydrating a solution in powder form by evaporating the solvent (usually water) by passing it through a stream of hot air. Firstly, sprayers are used to spray the solution in the form of fine droplets in the upper part of a tower called an atomisation chamber. At the same time, these fine droplets meet a counter-current flow of hot air, allowing the solvent to evaporate and dry up. In this type of installation, there are three characteristic zones:
 a drying tower including the atomisation chamber,
 a cyclone, and
 an internal and/or external fluidised bed.

Three types of sprayers can be used: centrifugal impeller, liquid pressure nozzles, bi-fluid nozzle.

With centrifugal impellers, the liquid is fed to the center of a turbine driven by gears. The centrifugally loaded liquid is ejected in fine droplets.

With nozzles under liquid pressure, spraying is carried out by passing the liquid through an orifice, the dispersion energy being provided by the liquid itself, which is conveyed under pressure.

Finally, with bi-fluid nozzles, the liquid is supplied at a relatively low pressure. Droplet dispersion is achieved by a high-speed jet of compressed air.

Atmospheric air is sucked in through filters adapted to the local conditions and the product to be dried. The air can be heated in two ways: by direct heating (electricity, gas) or indirect heating (water vapour, oil, gas).

There are two types of atomiser, single effect and multiple effects.

A "single-effect" or "one-time" atomisation implies a very short holding time in the drying tower (20-60 seconds). For the so-called "single effect" towers, the liquid is dried in the heat flow and then recovered at the bottom of the tower at the cyclone or bag filter. There's only one passage in the heat flow. The first generations of these towers are flat-bottomed. In the second generation, the bottom becomes conical shaped.

A single-effect atomiser, does not allow granulation of the atomised powder. After passing through the atomisation chamber, it is sent directly to the bottom of the tower to the static fluidised bed. The powder obtained is therefore of relatively small particle size.

The powders obtained are of fine quality and generally have a fair flow.

A "multiple effects" or "two-step" atomisation implies a longer holding time (a few minutes) and is thus closer to thermodynamic equilibrium. For the so-called "multiple effect" towers, after spraying the solution into the top of the atomisation chamber, the lightest particles (less than 50 μm), the fine ones, remain in the upper part of the tower and are carried by the air flow towards the cyclone. At the outlet, they can be returned to the atomisation chamber, where they meet the fine droplets of sprayed solutions and create clusters of different sizes, which then allow the powder to be granulated. The heavier particles are directed onto the static fluidised bed located in the lower part of the tower. At this stage, the solid particles still have residual moisture, which would not allow direct conditioning at the outlet of the tower. For this reason, a flow of hot air is directed under the fluidised bed allowing the wet powder to be cleaned and suspended to finish the drying stage.

A second fluidised bed can be integrated into the atomisation chain in the form of an external vibrating bed, also called vibrofluidizer, positioned just after the atomisation chamber. It finalises the drying process of the formed powder while cooling it to allow conditioning at a maximum temperature of 50° C., preferably between 25-35° C.

The powder obtained has a better flow (fluidity) and solubility than a powder obtained without granulation, because the particle size is greater and the contact surface between the liquid and the hot air flow is larger. A greater particle size also makes it possible to reduce the presence of powdery particles and thus improve the working conditions of the operators and reduce possible risks of explosion.

Preferably, the atomisation carried out according to the invention is a multiple-effect atomisation in bi-fluids.

The method according to the invention makes it possible to obtain a preferably biological extract titrated in at least 5% of rosmarinic acid without using a solvent, with an advantageous ratio of 7-10/1 (plant/final titrated product).

The second objective of the invention concerns a granulated or finely powdered extract containing at least 5% (w/w), advantageously 5-10%, of rosmarinic acid in weight with respect to the total weight of the extract obtainable through the method according to the invention and described above, from fresh plant material selected from the fresh aerial parts, flowering tops, flowers and/or leaves of plants from the Lamiaceae family.

The extract according to the invention is more preferably obtained from a plant material selected from sage (*Salvia* ssp), rosemary (*Rosmarinus officinalis*), oregano (*Origanum vulgare*), mint (*Mentha piperita*), summer savory (*Satureja hortensis* L.), lemon balm (*Melissa officinalis* L.), preferably from rosemary, oregano, lemon balm.

Such extracts are very difficult to characterise as such because they vary according to the plant material used, between two plant species, and also for the same species, according to different factors such as the parts used, the place of harvest, or the year of harvest.

A granule, or powder, means a collection of heterogeneous solid particles, generally less than one millimeter in size, dispersed in a continuous gaseous phase. Granular media have a particular behaviour that falls somewhere between solids and liquids.

Among the behaviours that a powder can exhibit, flowability is one of the most interesting for industrialists.

In terms of particle size measurement, powders can be classified in two categories: large size powders called "granules" (over 100 μm), for which the force of gravity outweighs the forces of cohesion, and which therefore flow easily; and conversely for small size "fine" powders (less than or equal to 100 μm), the flow of which is difficult.

Preferably, the extract obtained according to the invention should be in granulated form.

Another objective of the invention concerns a composition comprising, in a physiologically acceptable medium, an extract obtained through the method according to the invention.

A physiologically acceptable medium means a medium suitable for use in contact with human and animal cells, in particular epidermal cells, free from toxicity, irritation, undue allergic response and similar, and is proportionate to a reasonable benefit/risk ratio.

Such a physiologically acceptable medium may include excipients known and used in cosmetic and pharmacological fields. The skilled person shall take care to choose the physiologically acceptable medium so that it does not interfere with the interesting properties of the extract and the compositions according to the invention.

The composition according to the invention comprises between 0.1% and 100%, preferably 0.3 to 96%, of the extract in granulated or fine powder form, preferably granulated, containing at least 5% rosmarinic acid, e.g. 1%, 10%, or 50%, in weight of the total weight of the composition.

The composition according to the invention is formulated in a form suitable for oral administration or for topical application to the skin, preferably for oral administration.

The composition according to the invention may be in various forms acceptable for topical application, in particular in solid or liquid form, depending on the physiologically acceptable medium used.

The topical composition may be in the form of a water-in-oil (W/O) or oil-in-water (O/W) type emulsion, suspension, gel, paste, cream, lotion, solution, e.g. an aqueous, alcoholic, aqueous-alcoholic or fatty solution or even a powder.

The composition according to the invention may be formulated for oral administration. The galenic forms used may be in solid or liquid form. Solid oral forms are usually tablets, hard pills (capsules), soft capsules, sachets containing powder or granules. Oral liquid forms are usually oral solutions, syrups, elixirs, oral emulsions, oral suspensions or oral drops.

Finally, another objective of the invention concerns the uses of the compositions according to the invention.

The extract obtainable according to the method of the invention is enriched in rosmarinic acid (at least 5% w/w). Rosmarinic acid has sedative, antispasmodic, carminative, antimutagenic, antibacterial, antiviral, anti-inflammatory and especially antioxidant properties.

The compositions according to the invention are used in food and cosmetic fields.

The compositions according to the invention, depending on the patient, may also be intended for use in the pharmaceutical field, in phytotherapy or in animal health, in particular for their antioxidant properties as a nutraceutical or medicinal product in humans and/or animals.

The compositions can be advantageously used to treat headaches, anxiety, gastrointestinal disorders, bronchitis, depression, hysteria, rheumatism, flatulence, nausea, anaemia, vertigo, fainting, asthma, amenorrhoea, heart failure, heart conduction disorders, insomnia, epilepsy, psychosis, ulcers and injuries.

They can also be used in the prevention of Alzheimer's disease, thanks to their ability to inhibit acetylcholinesterase and their antioxidant activity.

More particularly, in phytotherapy, the compositions according to the invention may be used for their beneficial choleretic, antispasmodic, mild sedative, carminative, sympatholytic or antidepressive effect.

As an illustrative example, examples of formulations of a composition containing a rosmarinic acid-enriched extract obtained according to the invention are given below:

Example 1: Anti-Wrinkle Cream

| ingredients (INCI) | % (w/w) (in weight of total weight) |
|---|---|
| Pre-mix A | |
| C12-15 alkyl benzoate | 20 |
| PEG-75 lanolin | 4 |
| Ceteareth-12 | 1.5 |
| Cetyl alcohol | 2 |
| Petrolatum | 3 |
| Pre-mix B | |
| Water (aqua) | qsp 100% |
| Carbomer | 26.7 |
| Propylene glycol | 8 |
| Disodium EDTA | 0.05 |
| Glycerin | 2 |
| Propylene glycol, diazolidinyl urea, methylparaben and propylparaben | 1 |
| Pre-mix C | |
| Water (aqua) | 5 |
| Triethanolamine | 0.7 |
| Pre-mix D | |
| Fragrance | 0.5 |
| Lemon balm extract obtained according to the invention | 0.3 |

Example 2: Capsule

| ingredients (INCI) | Dose (mg/day) |
|---|---|
| SOD B ® (freeze-dried melon juice concentrate naturally rich in SuperOxide Dismutase (SOD)) | 10 |
| Lemon balm extract obtained according to the invention | 250 |

The invention is also illustrated below, without any limitation, through examples of preferred methods of execution.

Figure 1:
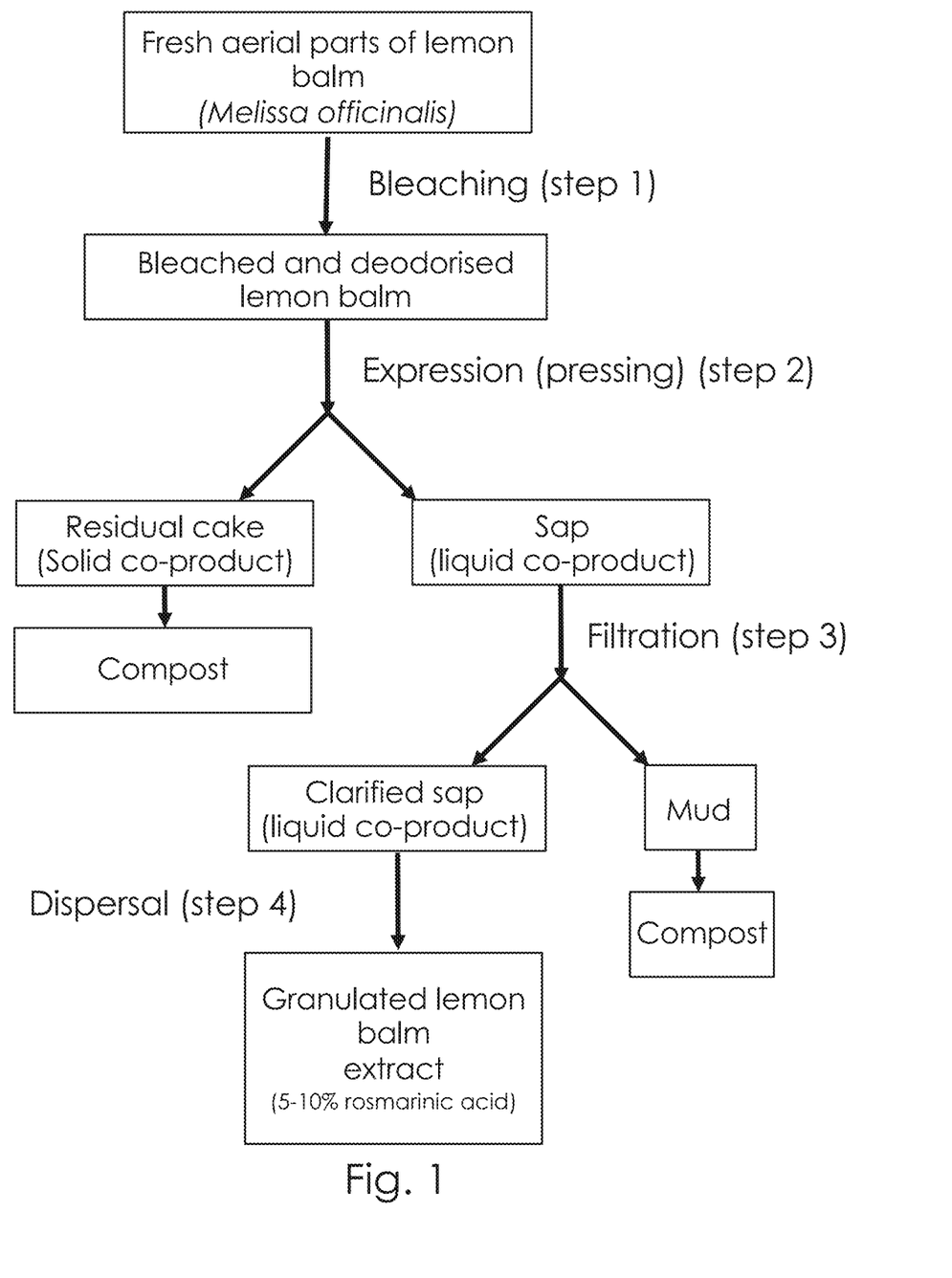
FIG. 1 represents a diagram of a method on how to carry out the method of obtaining an extract of lemon balm (*Melissa officinalis* L.) from fresh aerial parts of lemon balm according to the invention.

Example 3: Method for Obtaining a Rosmarinic Acid-Enriched Extract and Associated HPLC/DAD Results As shown in FIG. 1, 1 ton of fresh aerial parts of organically grown lemon balm (*Melissa officinalis* L.) is bleached 1 hour after harvesting, using steam at 100° C. for 15 min-1 h (step 1).

200 kg of sap (liquid co-product) are obtained after continuous expression at a temperature above 40° C., or around 60° C., with at least one compression screw, under a pressure of between 4 and 10 bar, for example 6 bar, of the bleached plant material (yield=20% between fresh plant and sap) (step 2).

The sap once obtained is then filtered by rotary filtration with a 100 µm self-cleaning filter to obtain a clarified sap with 20% loss, i.e. recovery of 160 kg of clarified sap (step 3).

The recovered clarified sap is finally atomised. Once the lemon balm solution has been prepared (clarified sap), it is then fed and sprayed into the atomisation chamber by means of 3 bi-fluid nozzles. The bi-fluid nozzles allow the solution to be delivered to the top of the tower at low pressure by a co-current jet of compressed air. On encountering the hot air current (170 to 200° C.) at the top of the tower, the water contained in the droplets of lemon balm solution is evaporated, leading to the formation of solid particles. In multiple-effect atomisation, the finest particles, smaller than 50 µm, remain at the top of the atomisation chamber and are carried by the air stream (60 to 100° C.) into the cyclone. They are then redirected into the chamber, allowing the granulation of the solid particles. The larger particles fall onto the static bed, where a flow of hot air (60 to 100° C.) completes the drying process of the lemon balm particles.

A brown granulated deodorised powder is thus obtained comprising 45-65% of particles larger than 400 µm, 30-50% of particles between 200 µm-400 µm and 0-10% of particles between 100 µm-200 µm, with an atomisation output of about 70-80% (step 4).

Figure 2:
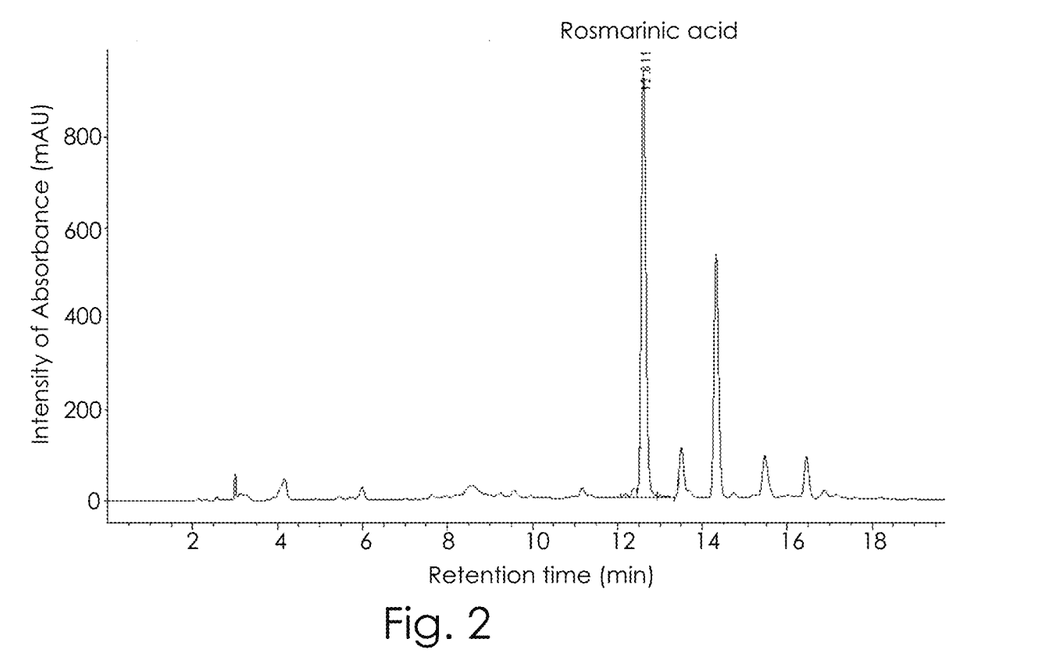
FIG. 2 represents an HPLC-DAD spectrum result showing the characteristic peak of rosmarinic acid contained in a lemon balm extract obtained according to the invention.

The compound content of the extract thus obtained is illustrated by the HPLC/DAD results of the spectrum in FIG. 2.

A sample of the extract obtained according to example 3 diluted in a solvent 70% EtOH96/30% $H_2O$ at a concentration of 7.1 mg/ml was analysed with an HPLC column NUCLEODUR™ C18 HTec EC (particle size [µm]: 5.0; length [mm]: 250; internal diameter [mm]: 4.6.

Under the chromatographic conditions used (volume injected [µl]: 10; flow rate of the mobile phase [ml/min]: 1; Temperature [° C.]: 35; Detection [nm]: 285), a characteristic peak of rosmarinic acid (8.2%) is observed at a retention rate of 12.611 minutes.

As shown in FIG. 1, value can also be added to the co-products (cake and mud) obtained from the method according to the invention and used as compost.

The results obtained confirm that the extracts (granules) obtainable through the method according to the invention contain at least 5%, advantageously between 5-10%, of rosmarinic acid in weight with respect to the total weight of the extract.

Such extracts and the compositions comprising them benefit from the known advantageous properties of rosmarinic acid in particular, such as sedative, antispasmodic, carminative, antimutagenic, antibacterial, antiviral, anti-inflammatory and especially antioxidant properties.

The compositions according to the invention can thus have an improved antioxidant effect and be used in the food (as a food supplement) and cosmetic fields and, depending on the patient, can also be used in the pharmaceutical field, as nutraceuticals, in phytotherapy or in animal health, in particular for their antioxidant properties.

Example 4: Method for Obtaining an Extract of Oregano (*Origanum vulgare* L.)

As an example, 300 kg of fresh aerial parts of organically grown oregano (*Origanum vulgare* L.) are bleached 1 hour after harvesting, using steam at 100° C. for 15 min-1 h (step 1).

60 kg of sap (liquid co-product) are obtained after continuous expression above 40° C., with at least one compression screw under pressure between 4 and 10 bar, e.g. 6 bar, of the bleached plant material (yield of around 20% between fresh plant and sap) (step 2).

The sap is filtered over 100 µm by rotary filtration to obtain a clarified sap with a loss of 10%, i.e. a recovery of 54 kg of clarified sap ready to be flash pasteurised (step 3).

The juice obtained is titrated between 0.3 and 1% of rosmarinic acid, preferably 0.5% and 1%; its dry matter content may vary between 3 and 12%, preferably between 4 and 10%. As an example, we obtained a clarified sap with 5% dry matter.

The recovered clarified sap is finally atomised and dosed under the same conditions as in Example 3.

The rosmarinic acid content of the oregano extract thus obtained is more than 5%, preferably more than 8%. As an example, we obtained a capacity with 9.8% of the extract's total weight being rosmarinic acid.

Example 5: Method for Obtaining an Extract of Rosemary (*Rosmarinus officinalis* L.)

As an example, 100 kg of fresh aerial parts of organically grown rosemary (*Rosmarinus officinalis* L.) is bleached 1 hour after harvesting, using steam at 100° C. for 15 min-1 h (step 1).

35 kg of sap (liquid co-product) are obtained after continuous expression above 40° C., with at least one compression screw under pressure between 4 and 10 bar, e.g. 6 bar, of the bleached plant material (yield of around 35% between fresh plant and sap) (step 2).

The sap is filtered over 100 µm by rotary filtration to obtain a clarified sap with a loss of 10%, i.e. a recovery of 31.5 kg of clarified sap ready to be flash pasteurised (step 3).

The sap obtained is titrated between 0.3 and 1% rosmarinic acid, preferably 0.5% and 1%. As an example, the rosmarinic acid content obtained is 0.51%; its dry matter content can vary between 3 and 12%, preferably between 5 and 10%. As an example, we obtained 8.5% dry matter.

The recovered clarified sap is finally atomised and dosed under the same conditions as in Example 3.

The rosmarinic acid content of the rosemary extract thus obtained is more than 5%. As an example, we obtained a concentration of 5.7% of rosmarinic acid in weight in relation to the total weight of the extract.

In this respect, the invention is illustrated hereafter by the results of antioxidant activity tests.

Example 6: Measurement of the Antioxidant Activity of a Lemon Balm Extract Obtained According to the Invention with PAOT Technology®

Antioxidants are molecules of various origins capable of neutralising activated and toxic forms of oxygen (singlet oxygen, superoxide anion, hydrogen peroxide and peroxyl radicals, hydroxyl radical) and slowing the degradation of certain materials or organic compounds following the effects of oxidation.

Total antioxidant activity is the ability of an antioxidant compound or set of antioxidant compounds to scavenge free radicals. It can be evaluated using various classic measurement techniques (DPPH; TEAC (ABTS), ORAC, FRAP) and with a modern method (developed by the European Antioxidant Institute IEA) "PAOT Liquid Technology®": Total Antioxidant Power.

PAOT Technology® is more accurate because it measures all the antioxidant molecules present in the extract, unlike other classic tests. This can be explained by the fact that standard methods do not take into account the nature and specificity of antioxidants and the interaction between the solvent and the extract.

PAOT Technology® is a method for directly measuring the total antioxidant and oxidative activity of various products such as raw food materials (fruit/vegetables, tea), processed food products, as well as cosmetic and medicinal preparations.

The PAOT/POT® technology (Total Antioxidant Power/Total Oxidant Power) is based on the electrochemical nature of the oxidation-reduction reactions (antioxidants/oxidants balance). The principle is based on potentiometry, i.e. the change in the ratio of oxidised and reduced forms of the components of the medium. This change is a result of the variation in the concentrations of the oxidised/reduced forms during the reaction (1) for the antioxidants and the reaction (2) for the oxidants:

Reaction medium+AO (Antioxidant)→Reaction medium+AO Ox (Antioxidant oxidation result) (1)

Reaction medium+OA (Oxidant)→Reaction medium+OA Red (Result of oxidant reduction) (2)

The total antioxidant power of a product is expressed in PAOT Score® units (PAOT Score/l or PAOT Score®/g of product), which measures a product's ability to neutralise free radicals. This index is used to select the products that provide the best antioxidant protection. It is obtained by PAOT Technology® and can be expressed in relation to reference antioxidants.

Experimental conditions were carried out in triplicate (n=3). The results obtained (PAOT® score) are compiled in the table below:

| | Unit | PAOT Score® 1 | PAOT Score® 2 | PAOT Score® 3 | Average | Standard deviation |
|---|---|---|---|---|---|---|
| Lemon balm extract according to the invention (example 3) | g | 2.25 | 2.3 | 2.27 | 2.27 | 0.0278 |

Under these conditions, the extract of lemon balm according to the invention (sample from the extract obtained according to example 3) obtains an average PAOT® score of 2.27/g (Standard deviation=0.03).

The antioxidant activity of lemon balm extract according to the invention is compared with that of known antioxidant compounds. Equivalence is expressed in g of reference per gram of product. The higher the equivalence value, the higher the efficacy of the product.

For the analysis, 1 g of product is tested purely using the PAOT Liquid Technology® probe. The results obtained are compiled in the table below and illustrated in FIG. 3.

| Lemon balm extract according to the invention (example 3) | In Trolox equivalent (g) | In Ascorbic Acid Equivalent (g) | In BHA equivalent (g) | In BHT equivalent (g) | In equivalent aTocopherol (g) |
|---|---|---|---|---|---|
| Trial 1 | 2.81E−01 | 1.93E−01 | 2.18E−01 | 2.47E−01 | 4.83E−01 |
| Trial 2 | 2.88E−01 | 1.98E−01 | 2.23E−01 | 2.53E−01 | 4.95E−01 |
| Trial 3 | 2.83E−01 | 1.95E−01 | 2.20E−01 | 2.49E−01 | 4.88E−01 |
| Average | 2.84E−01 | 1.95E−01 | 2.20E−01 | 2.50E−01 | 4.89E−01 |
| Standard deviation | 3.48E−03 | 2.40E−03 | 2.70E−03 | 3.07E−03 | 6.00E−03 |

Figure 3:
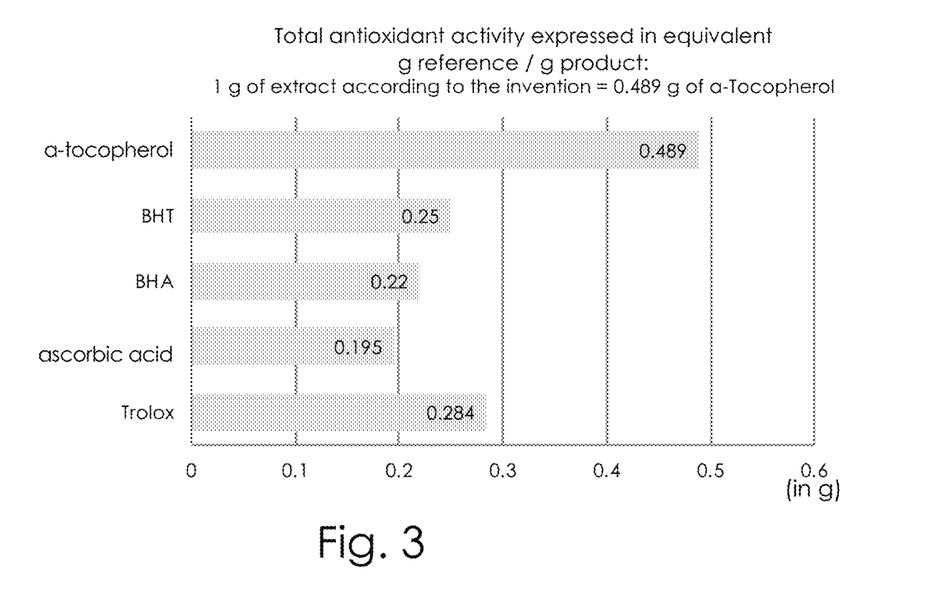
FIG. 3 represents a comparative measurement with PAOT Technology® of the antioxidant activity of a lemon balm extract obtained according to the invention compared to that of known antioxidants.

As shown in FIG. 3, the total antioxidant power (PAOT®) of 1 gram of lemon balm extract according to the invention is thus equivalent to that of 489 mg of vitamin E (a-tocopherol), 195 mg of vitamin C (ascorbic acid), 284 mg of Trolox, 220 mg of butylated hydroxyanisole (BHA) and 250 mg of butylhydroxytoluene (BHT).

The extract according to the invention therefore has antioxidant activity as revealed by the in vitro test of PAOT liquid Technology®.

The invention claimed is:

1. A method for obtaining an extract enriched in rosmarinic acid from fresh plant material selected from the fresh aerial parts, flowering tops, flowers and/or leaves of plants from sage (*Salvia* ssp), rosemary (*Rosmarinus officinalis*), oregano (*Origanum vulgare*), mint (*Mentha piperita*), summer savory (*Satureja hortensis* L.), and lemon balm (*Melissa officinalis* L.), the method comprising:

1) steam bleaching said plant material for a period lasting between 1 minute and 1 hour at atmospheric pressure at a temperature of 100° C.;
2) continuous expressing with at least one compression screw, under pressure between 4 and 10 bar, of the plant material bleached in 1) with recovery of a sap;
3) filtering the sap recovered in 2) to produce a clarified sap; and
4) atomizing the clarified sap to obtain a granulated or finely powdered extract containing at least 5% of rosmarinic acid in weight relative to the total weight of the extract.

2. The method according to claim 1, wherein expressing is carried out with a compression screw at a power of at least 7.5 kW.

3. The method according to claim 1, wherein filtering is by rotary filtration carried out with a 100 μm self-cleaning filter.

4. The method according to claim 1, wherein atomizing is by multiple-effect atomisation into bi-fluids.

5. The method according to claim 1, wherein the plant material is selected from rosemary, oregano, and lemon balm.

6. The method according to claim 5, wherein the plant material is lemon balm.

\* \* \* \* \*